(12) United States Patent
Liu et al.

(10) Patent No.: US 8,326,547 B2
(45) Date of Patent: Dec. 4, 2012

(54) METHOD OF SEQUENCE OPTIMIZATION FOR IMPROVED RECOMBINANT PROTEIN EXPRESSION USING A PARTICLE SWARM OPTIMIZATION ALGORITHM

(75) Inventors: Xiaowu Liu, Nanjing (CN); Yun He, Nanjing (CN); Zhuying Wang, Monmouth Junction, NJ (US); Chunjiao Wang, Nanjing (CN); Zhibing Liu, Nanjing (CN); Tianhui Xia, Edison, NJ (US); Luquan Wang, East Brunswick, NJ (US); Fang Liang Zhang, Fanwood, NJ (US)

(73) Assignee: Nanjingjinsirui Science & Technology Biology Corp., Nanjing (CN)

( * ) Notice: Subject to any disclaimer, the term of this patent is extended or adjusted under 35 U.S.C. 154(b) by 114 days.

(21) Appl. No.: 12/894,401

(22) Filed: Sep. 30, 2010

(65) Prior Publication Data

US 2011/0081708 A1    Apr. 7, 2011

Related U.S. Application Data

(60) Provisional application No. 61/249,411, filed on Oct. 7, 2009.

(51) Int. Cl.
*G06F 19/10*    (2011.01)
*G06F 19/00*    (2011.01)

(52) U.S. Cl. ............................................. 702/19; 702/20

(58) Field of Classification Search .......................... None
See application file for complete search history.

(56) References Cited

OTHER PUBLICATIONS

Cai et al. (Journal of Theoretical Biology (2008) vol. 254, pp. 123-127).*
Khalid et al. (Prosiding Simposium Kebangsaan Sains Matematik ke-16 (2008) Jun. 205; pp. 1-11).*
Shen et al.( Computational Biology and Chemistry (2008) vol. 32; pp. 53-60).*
Xiao et al. (Concurrency and Computation: Practice and Experience (2004) vol. 16; pp. 895-915).*
Khalid et al. (Second Asia International Conference on Modelling and Simulation; IEEE Computing Society (2008); AICMS, 08; ACM, Kuala Lumpur, Malaysia).*
O'Neill et al. (Congress on Evolutionary Computation (2004) CEC, 2004, Jun. 19-23, 2004, vol. 1; pp. 104-110).*
Rouchka et al. (BMC Bioinformatics (2007) vol. 8; pp. 292-299).*
Zhang et al. (The 1st International Congress on Bioinformatics and Biomedical Engineering (2007) ICBBE 2007, Jul. 6-9, 2007; pp. 53-56).*

* cited by examiner

*Primary Examiner* — Lori A Clow
(74) *Attorney, Agent, or Firm* — Panitch Schwarze Belisario & Nadel LLP

(57) ABSTRACT

An improved gene sequence optimization method, the systematic optimization method, is described for boosting the recombinant expression of genes in bacteria, yeast, insect and mammalian cells. This general method takes into account of multiple, preferably most or all, of the parameters and factors affecting protein expression including codon usage, tRNA usage, GC-content, ribosome binding sequences, promoter, 5'-UTR, ORF and 3'-UTR sequences of the genes to improve and optimize the gene sequences to boost the protein expression of the genes in bacteria, yeast, insect and mammalian cells. In particular, the invention relates to a system and a method for sequence optimization for improved recombinant protein expression using a particle swarm optimization algorithm. The improved systematic optimization method can be incorporated into a software for more efficient optimization.

20 Claims, 1 Drawing Sheet

METHOD OF SEQUENCE OPTIMIZATION FOR IMPROVED RECOMBINANT PROTEIN EXPRESSION USING A PARTICLE SWARM OPTIMIZATION ALGORITHM

CROSS-REFERENCE TO RELATED APPLICATIONS

This application claims the benefit under 35 U.S.C. §119 (e) of U.S. Provisional Application No. 61/249,411, filed Oct. 7, 2009, the entire disclosure of which is hereby incorporated herein by reference.

FIELD OF THE INVENTION

The invention relates to recombinant protein expression in bacterial, yeast, insect or mammalian cells. In particular, the invention relates to a system and a method for sequence optimization for improved recombinant protein expression using a particle swarm optimization algorithm.

BACKGROUND OF THE INVENTION

Recombinant protein expression has become a major tool to analyze intracellular processes. The expression of foreign genes in transformed organisms is now an indispensable method for purification of the proteins for subsequent uses, such as protein characterization, protein identification, protein function and structure study, etc. Proteins are also needed to be expressed at large scale to be used as enzymes, as nutritional proteins and as biopharmaceuticals (drugs). Escherichia coli (E. coli) is one of the most widely used protein expression host system because it allows rapid expression and subsequent large-scale, cost-effective manufacturing of the recombinant proteins. While most prokaryotic genes are readily expressed in a prokaryotic expression system, such as E. coli, many eukaryotic genes cannot be expressed efficiently in a prokaryotic system. The completion of the human genome sequencing project has led to a rapid increase in genetic information, with tens of thousands of new proteins waiting to be expressed and explored. Efficiently expressing these proteins in a recombinant system, such as an E. coli cell, for further study and use has become a pressing issue.

Many sequence factors, such as codon usage, mRNA secondary structures, cis-regulatory sequences, GC content and other similar variables affect protein expression (Villalobos et al, 2006, "Gene Designer: a synthetic biology tool for constructing artificial DNA segments," *BMC Bioinformatics* 7, 285). Methods have been developed to optimize one or more sequence elements to improve protein expression. For example, it has been demonstrated that codon optimization can increase protein expression level (Pikaart et al., 1996, Expression and codon usage optimization of the erythroid-specific transcription factor cGaTA-1 in baculoviral and bacterial systems, *Protein Expression and Purification*, vol. 8, pp. 469-475; and Hale et al., 1998, Codon optimization of the gene encoding a domain from human type 1 neurofibromin protein results in a threefold improvement in expression level in *Escherichia coli*, *Protein Expression and Purification*, vol. 12, pp. 185-188). However, the prior art methods are generally limited to the optimization of a particular sequence factor, e.g., codon usage, that improves recombinant expression of a particular protein in a specific host cell. There remains a need of a general method for sequence optimization that takes into account of multiple or all sequence factors and is applicable for improved expression of any protein in any host cell.

Particle Swarm Optimization (PSO) is a population based stochastic optimization technique modeled on swarm intelligence that finds a solution to an optimization problem in a search space or model and predicts social behavior in the presence of objectives. It was first developed by Dr. Eberhart and Dr. Kennedy in 1995, inspired by social behavior of bird flocking or fish schooling (*Proceedings of the IEEE International Conference on Neural Networks*, 1942-948). In PSO, the potential solutions, called particles, fly through a multi-dimensional problem space by following the current optimum particles. Each particle keeps track of its coordinates (position and velocity) in the problem space which are associated with the best solution (fitness) it has achieved so far, the local best. Each particle also tracks the "best" value obtained so far by any particle in the neighbors of the particle, the neighboring best. When a particle takes all the population as its topological neighbors, the best value is a global best, which is known to all and immediately updated when a new best position is found by any particle in the problem space.

The particle swarm optimization concept consists of, at each time step, changing the velocity of each particle toward its local best and neighboring best locations. The change in velocity is weighted by a random term, with separate random numbers being generated for change in velocity toward its local best and neighboring best locations.

It is demonstrated that PSO gets better results in a faster, cheaper way compared with other methods. In addition, there are few parameters to adjust in PSO algorithm. PSO can be used across a wide range of applications, as well as for specific applications focused on a specific requirement. In the past several years, PSO has been successfully applied in several research and application areas. For example, PSO has been successfully applied in research and application areas such as bellow optimum design (Ying et al, 2007, Application of particle swarm optimization algorithm in bellow optimum design, *Journal of Communication and Computer*, 32, 50-56). It has also been used for optimization of codon usage (Cai et al, 2008, Optimizing the codon usage of synthetic gene with QPSO algorithm, *Journal of Theoretical Biology*, 254, 123-127).

Despite the exhaustive effort of protein expression researchers and ever-increasing knowledge of protein expression, significant obstacles remain when one attempts to express a foreign or synthetic gene in a protein expression system such as E. coli. There is a need of a faster and simpler systematic sequence optimization method that coordinates various sequence factors, resulting in improved protein expression in a recombinant system. Such a method is described here.

BRIEF SUMMARY OF THE INVENTION

In one general aspect, embodiments of the present invention relate to a method for optimizing a gene sequence for expression of a protein in a host cell. The method comprises:

(a) identifying a plurality of sequence factors that affect the expression of the protein in the host cell;

(b) defining a particle swarm optimization algorithm comprising a function for each of the plurality of sequence factors; and (c) applying the particle swarm optimization algorithm to the gene sequence to obtain an optimized gene sequence for expression of the protein in the host cell, wherein the optimized gene sequence takes into account of the plurality of sequence factors and achieves the maximum value of the swarm optimization algorithm, wherein at least the applying step is performed on a computer.

In another general aspect, embodiments of the present invention relate to a system for optimizing a gene sequence for expression of a protein in a host cell. The system comprises a computer system for applying a particle swarm optimization algorithm to the gene sequence to obtain an optimized gene sequence for expression of the protein in the host cell, wherein the particle swarm optimization algorithm comprises a function of each of a plurality of sequence factors that affect the expression of the protein in the host cell, the optimized gene sequence takes into account of the plurality of sequence factors and achieves the maximum value of the swarm optimization algorithm.

In yet another general aspect, the present invention relates to a program product stored on a recordable medium for optimizing a gene sequence for expression of a protein in a host cell. The program product comprises a computer software for applying a particle swarm optimization algorithm to the gene sequence to obtain an optimized gene sequence for expression of the protein in the host cell, wherein the particle swarm optimization algorithm comprises a function of each of a plurality of sequence factors that affect the expression of the protein in the host cell, the optimized gene sequence takes into account of the plurality of sequence factors and achieves the maximum value of the swarm optimization algorithm.

In a preferred embodiment of the present invention, the particle swarm optimization algorithm is defined as:

$$F(x) = f_{total}(x) - \sum_{i=1}^{p} \omega_i \times f_i(x) \quad (1)$$

wherein, $$f_{total}(x) = S_{codon} \times n \quad (2)$$

$f_{total}(x)$ is an initiation total score of the gene sequence; total n is the length of the protein; and $S_{codon}$ represents a function of codons within the protein;

p is the number of the identified plurality of sequence factors and p>1;

$f_i(x)$ denotes a function of the $i^{th}$ sequence factor of the identified p sequence factors; and $\omega_i$, denotes the relative weight given to $f_i(x)$;

wherein the optimized gene sequence achieves the maximum value of F(x).

In another embodiment, the plurality of sequence factors are comprised of GC-content, CIS elements, repetitive elements, RNA splicing sites, ribosome binding sequences, Promoter, 5'-UTR, ORF and 3'-UTR sequences of the genes, etc.

Other aspects of the invention relate to a method of expressing a protein using the optimized gene sequence obtained from a method of the present invention, an isolated nucleic acid molecule comprising the optimized gene sequence, and a vector or a recombinant host cell comprising the isolated nucleic acid.

The details of one or more embodiments of the disclosure are set forth in the accompanying drawings and the description below. Other features, objects, and advantages will be apparent from the description and drawings, and from the claims.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited by the drawings.

In the drawing.

DETAILED DESCRIPTION OF THE INVENTION

Figure 1:
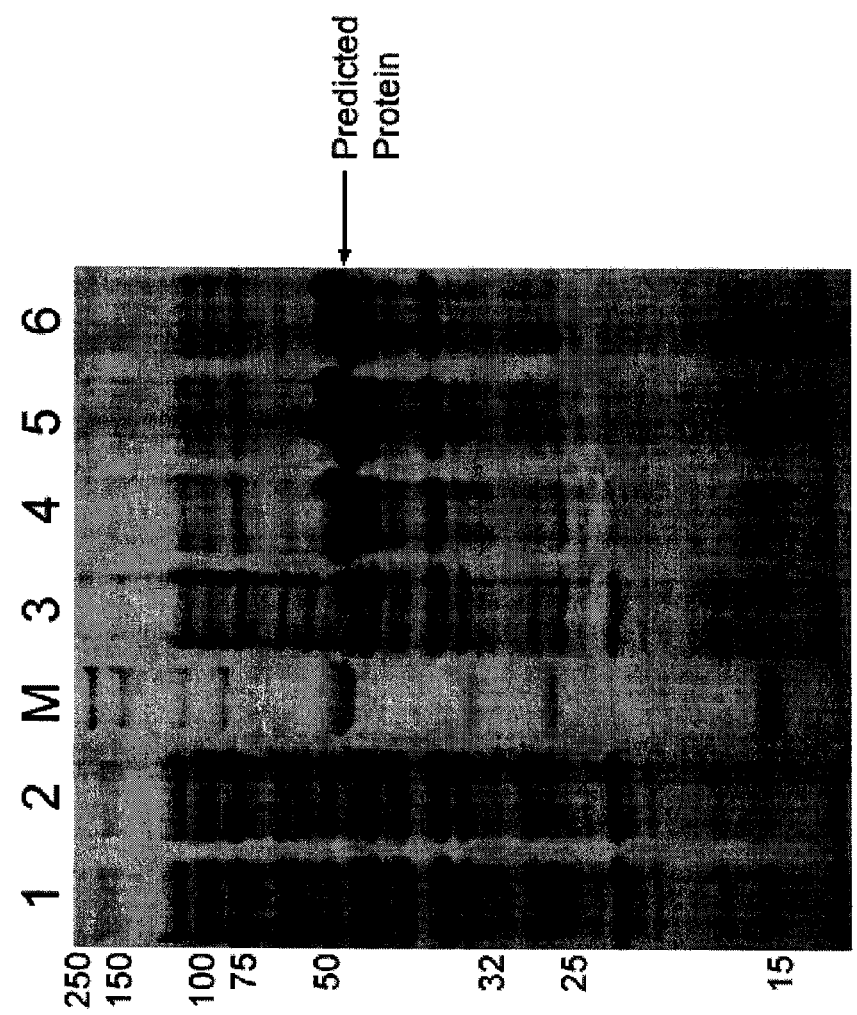
FIG. 1 is a picture of a SDS-PAGE gel after Coomassie Blue Staining, which illustrates recombinant expression in *E. coli* cells of the human OCT 4 gene: Lanes 1-2 contained cell lysates from cells transformed with human OCT 4 gene sequence without any sequence optimization, the cells were gown under conditions for induced expression of the OCT 4 gene; Lane 3 contained cell lysate from cells transformed with human OCT 4 gene sequence optimized by systematic optimization according to an embodiment of the present invention, the cells were gown under conditions for non-induced expression of the optimized OCT 4 gene; Lanes 4-6 contained cell lysates from the same cells as that used in Lane 3, except that the cells were gown under conditions for induced expression the optimized OCT 4 gene; and Lane M contains protein markers with the molecular weight shown on the left side of the picture.

Unless defined otherwise, all technical and scientific terms used herein have the same meaning as is commonly understood by one of skill in the art to which this invention belongs. All publications and patents referred to herein are incorporated by reference.

The invention provides a method useful for performing gene sequence optimization to boost the protein expression of genes in expression host cells. In one aspect, the invention provides a significant improvement of the gene sequence optimization method for protein expression. The invention provides a systematic method whereby preferably all or most of the parameters and factors affecting protein expression including, but not limited to, codon usage, tRNA usage, GC-content, ribosome binding sequences, promoter, 5'-UTR, ORF and 3'-UTR sequences of the genes are taken into consideration to improve and optimize the gene sequences to boost the protein expression of genes in expression host cells. Omitting one or more factors or parameters from the consideration may result in low or no expression of the interest genes in the expression host cells.

According to embodiments of the present invention, an inventive particle swarm optimization algorithm is applied to accomplish the systematic optimization of gene sequences. This systematic approach represents a significant shift from the prior art approaches that focused on individual factors, such as codon optimization, mRNA secondary structures or other factors, thus results in great improvement in gene expression of recombinant proteins, particularly those that could not be optimally expressed using the conventional methods.

Protein expression is the translation of mRNA. To boost protein expression, the expressed proteins are preferably produced at high level and remain stable with no or very little degradation. To reduce or minimize the proteolytic degradation of the protein, host strains with several deficient protease genes are preferably used for protein expression. To produce high level of proteins, mRNA is preferably produced at high level, not degraded quickly, and is translated efficiently.

To reduce or minimize the mRNA degradation or increase the stability of mRNA thus to reduce the turnover time of mRNA, cis-acting mRNA destabilizing motifs including, but not limited to, AU-rich elements (AREs) and RNase recognition and cleavage sites is preferably mutated or deleted from the gene sequences. AU-rich elements (AREs) with the core motif of AUUUA (SEQ ID NO:3) are usually found in the 3' untranslated regions of mRNA. Another example of the mRNA cis-element consists of sequence motif TGYYGAT-GYYYYY (SEQ ID NO:2), where Y stands for either T or C. RNase recognition sequences include, but are not limited to, RNase E recognition sequence. A host strain with deficient RNases can also be used for protein expression.

RNase splicing sites can cause RNA splicing to produce a different mRNA and therefore reduce the original mRNA level. RNase splicing sites are also preferably mutated to non-functional to maintain the mRNA level.

To produce high level of mRNA, the optimal transcription promoter sequence is preferably used in the gene sequences. For prokaryotic host such as E. coli, one of the strong promoters is T7 Promoter for T7 RNA Polymerase (T7 RNAP). Some bases of long or short tandem simple sequence repeat (SSR) are preferably mutated using codon degeneracy to break the repeats to reduce polymerase slippage, to thus reduce premature protein or protein mutations.

There are additional factors and parameters that affect mRNA translation and the resulting protein expression level. These factors affect translation from translation initiation through translation termination. Ribosomes bind mRNA at the ribosome binding site (RBS) to initiate translation. Because ribosomes do not bind to double-stranded RNA, the local mRNA structure around this region is preferably single-stranded and not form any stable secondary structure. The consensus RBS sequence, AGGAGG (SEQ ID NO:1), for prokaryotic cells such as E. coli, also called Shine-Dalgarnon sequence, is preferably placed a few bases just before the translation start site in the genes to be expressed. However, internal ribosome entry site (IRES) is preferably mutated to prevent ribosomes binding to avoid non-specific translation initiation.

After translation initiation, ribosomes read the mRNA and enlist the tRNAs to transfer the correct amino acid building blocks to make proteins. Since there exist 61 codons to encode 20 naturally occurring amino acids and 3 additional codons (amber, ochre, opal) to encode one stop signal of translation, which is called "degeneracy of the genetic code", each amino acid can be coded by several different codons. Accordingly, the same amino acid can be transferred to ribosomes by several different tRNAs. However, the use of synonymous codons is strongly biased in both the prokaryotic and eukaryotic systems, comprising both bias between codons recognized by the same transfer RNA and bias between groups of codons recognized by different synonymous tRNAs (Michael Bulmer, 1987, Coevolution of codon usage and transfer RNA abundance, *Nature* 325, 728-730). Several statistical methods have been proposed for quantitatively analyzing codon usage bias. One of the most commonly used methods is codon adaptation index (CAI). Codon adaptation index is a measurement of the relative adaptiveness of the codon usage while the relative adaptiveness is calculated as the ratio of the usage of each codon to that of the most abundant synonymous codon for the same amino acid (Sharp P M and Li W H, 1987, The Codon Adaptation Index—a measure of directional synonymous codon usage bias, and its potential applications. *Nucleic Acids Research*, 15 (3), 1281-1295).

To boost protein translation efficiency, the gene sequences is preferably optimized so that codon usages are optimized according to the tRNAs abundance or the availability of the different tRNAs. Generally the optimal range for CAI is preferably from 0.8 to 1.0. A second method to quantitatively analyzing codon usage bias is codon context index (CCI) derived from "codon pair" theory (Irwin B, Heck J D and Hatfield G W, 1995, Codon pair utilization biases influence translational elongation step times. *Journal of Biological Chemistry*, 270 (39), 22801-22806) and the optimal range for CCI is preferably from 0.7 to 1.0.

The maximization of CAI or CCI is not enough to boost protein expression. In the traditional codon optimization methods, the most preferred codons are always selected, which will result in the quick exhaustion of the tRNAs of the most preferred codons and hence the subsequential decrease of the translation efficiency.

According to embodiments of the present invention, the codon diversity is also taken into account. The most preferred codons are used the most for codon optimization, however, less preferred codons are also used to increase the tRNA usage efficiency thus to increase translation efficiency, although to a less content.

The potential strong stem-loop secondary structures of mRNA located in the downstream of the start codon may hinder the movement of the ribosome complex, and thus slow down the translation and reduce the translation efficiency. The strong secondary structures of mRNA can even cause the ribosome complex to fall off the mRNA and result in the termination of translation. There are several methods for free energy calculation and secondary structure prediction. One of them is mfold program (Mathews et al., 1999, Expanded Sequence Dependence of Thermodynamic Parameters Improves Prediction of RNA Secondary Structure, *J. Mol. Biol.* 288, 911-940).

According to embodiments of the present invention, the local secondary structures of mRNA with a low free energy ($\Delta G < -18$ Kcal/mol) or a long complementary stem ($>10$ bp) are defined as too stable for efficient translation. The gene sequences is preferably optimized to make the local structure not so stable.

Both of the 5'-UTR and 3'-UTR of mRNA are preferably taken into consideration for mRNA structure free energy calculation and secondary structure prediction.

GC-content of mRNA is also preferably monitored. An ideal range for GC % is approximately 30-70%. High GC-content will make mRNAs to form strong stem-loop secondary structures. It will also cause problems for PCR amplification and gene cloning. The high GC-content of the target sequence is preferably mutated using codon degeneracy to be around 50-60%. There are two different measurements for GC %. One is the global GC % which is averaged along the whole sequence; the other is more useful, which is the local GC % calculated within a shifted "window" of fixed size (e.g. 60 bp).

According to embodiments of the present invention, the local GC % is optimized to around 50-60%.

Theoretically all the parameters and factors affecting gene expression, including those described above, can be taken into account to optimize the genes for optimal expression of the genes. For a short gene of a few hundred base pairs, it is possible to optimize the sequences of the genes manually by checking and modify the sequences using those parameters. However, most of the genes are much longer and even up to tens of thousands of base pairs. It is not possible to manually perform a systematic optimization of the gene sequences. Embodiments of the present invention tackle this problem using an inventive algorithm based on Particle Swarm Optimization (PSO) theory.

A novel POS algorithm was defined to systematically optimize gene sequences by taking into account multiple, preferably most or all, of those parameters and factors that affect gene expression.

An objective function, F(x), is defined as:

$$F(x) = f_{total}(x) - [\omega_1 \times f_1(x) + \omega_2 \times f_2(x) + \omega_3 \times f_3(x) + \psi_4 \times f_4(x) + \omega_5 \times f_5(x) + \omega_6 \times f_6(x) + \omega_7 \times f_7(x)] \quad (1)$$

Wherein $\omega_1$, $\omega_2$, $\omega_3$, $\omega_4$, $\omega^5$, $\omega_6$ and $\omega_7$ denote the relative weights given to $f_1(x)$, $f_2(x)$, $f_3(x)$, $f_4(x)$, $f_5(x)$, $f_6(x)$ and $f_7(x)$, respectively;

$$\text{And } f_{total}(x) = S_{codon} \times n \quad (2)$$

Wherein $f_{total}(x)$ is an initiation total score of optimized DNA sequence, n is the total length of protein sequence decoded by this DNA sequence, and $S_{codon}$ represents a score of codons;

$$\text{And } f_1(x) = \sum_{i=1}^{c1} \sum_{j=1}^{l1} d_{ij} \quad (3)$$

Wherein $f_1(x)$ scores the direct repeats in the optimized DNA sequence, c1 is occurrences of repetitive fragments, l1 is the length of repeats, and $d_{ij}$ represents the score of jth nucleotide of ith direct repeat;

$$\text{And } f_2(x) = \sum_{i=1}^{c2} \sum_{j=1}^{l2} r_{ij} \quad (4)$$

Wherein $f_2(x)$ scores the reverse repeats in the optimized DNA sequence, c2 is occurrences of reverse repetitive fragments, l2 is the length of reverse repeats, and $r_{ij}$ represents the score of jth nucleotide of ith reverse repeat;

$$\text{And } f_3(x) = \sum_{i=1}^{c3} \sum_{j=1}^{l3} dy_{ij} \quad (5)$$

Wherein $f_3(x)$ scores the dyad repeats in the optimized DNA sequence, c3 is occurrences of dyad repetitive fragments, l3 is the length of reverse repeats, and $dy_{ij}$ represents the score of jth nucleotide of ith dyad repeat;

$$\text{And } f_4(x) = \sum_{i=1}^{c4} \varepsilon_i \times s_{motif}^i \quad (6)$$

Wherein $f_4(x)$ scores the negative motifs in the optimized DNA sequence such as PolyA, restriction sites, C4 is occurrences of negative motifs, $\varepsilon_i$ is the corresponding weight given to ith motif, and $S^i_{motif}$ scores the ith negative motif;

$$\text{And } f_5(x) = \left( \prod_{i=1}^{n} (f_{ik}/f_{imax}) \right)^{\frac{1}{n}} \quad (7)$$

Wherein $f_5(x)$ measures the used codon bias of target gene sequence, $f_{ik}$ represents the frequency of the kth synonymous codon of ith amino acid, $f_{imax}$ represents max the codon with the most frequency in all synonymous codons of ith amino acid, and n is the length of protein sequence decoded by the DNA sequence;

$$\text{And } f_6(x) = \sum_{i=1}^{c6} (x_i)^{\alpha - s6} \quad (8)$$

Wherein $f_6(x)$ scores the undesirable splicing sites in the optimized gene sequence, c6 is the occurrences of the candidate splicing sites, $x_i$ is the base of score function, $\alpha$ is a threshold of scoring the splicing site, and s6 represents a score of the splice site evaluated by splicing site prediction system;

$$\text{And } f_7(x) = \sum_{i=1}^{l-w} \left| v_{gc} - \sum_{j=1}^{w} \frac{c_j}{w} \right|_i \quad (9)$$

Wherein $f_7(x)$ scores GC content with a fixed window in the optimized gene sequence, l is the length of target DNA sequence, $v_{gc}$ is the cutoff value of ideal GC content, and $c_j$ is the occurrence of base G and C, $c_j$ is 1 if jth nucleotide is G or C, otherwise, 0.

F(x) is an objective function that can be expanded to include multiple or all parameters or factors that affect gene expression. When the optimization is going on, the value of F(x) will go up until it reaches maximum, i.e., the global best, when the optimized sequence is obtained.

The invention therefore relates to a process for optimizing the gene sequences using the systematic method. The above objective functions, F(x) and $f_1(x)$ through $f_7(x)$, can be programmed into a software for easy operation. Using a computer loaded with the software, one can optimize a gene sequence for improved expression of the gene in a host cell, for example, by removing mRNA destabilizing motifs via mutating or deleting the motifs from the gene sequence to be expressed, adding the DNA sequences or motifs that enhance transcription or mRNA production to the gene sequence to be expressed, adding the DNA sequences or motifs that stabilize mRNA to the gene sequence to be expressed, placing the most favorable RBS sequences just before or a few bases before the translation start site in the gene to be expressed, optimizing the ORF sequences to maximize the codon usage efficiency, optimizing the gene sequences by using alternative codons until that the local mRNA structure around RBS region is single-stranded and not form any stable secondary structure to increase the translation efficiency to enhance translation, etc.

Within minutes, one can optimize a gene sequence with all the parameters and factors considered for optimal expression of the gene assisted by a computer loaded with a software executing a POS algorithm according to an embodiment of the present invention.

In the above-mentioned embodiments, in view of the present disclosure, those skilled in the art will know how to screen for cis-acting mRNA destabilizing motifs such as AU-rich elements (AREs), RNAse recognition and cleavage sites. Those skilled in the art will also know how to calculate CAI and the free energy of mRNA and mutate the gene sequences.

According to embodiments of the present invention, the systematic method to optimize gene sequences can be used for any protein expression systems such as that using bacteria, yeast, insect or mammalian cells as the host cells.

In one embodiment, the optimized gene sequence obtained by a method of the present invention can be synthesized, cloned into the host cell and expressed in the host cell for the production of the encoded protein.

Thus, another embodiment of the present invention relates to a method for expressing a protein in a host cell. The method comprises:

(a) obtaining an optimized gene sequence for expression of the protein in the host cell using a method according to an embodiment of the present invention;

(b) synthesizing a nucleic acid molecule comprising the optimized gene sequence;

(c) introducing the nucleic acid molecule into the host cell to obtain a recombinant host cell; and (d) cultivating the recombinant host cell under conditions to allow expression of the protein from the optimized gene sequence.

In view of the present invention, any method can be used to synthesize the nucleic acid molecule comprising the optimized gene sequence, e.g., by using a DNA synthesizer, by introducing mutations into an existing nucleic acid molecule, etc. In view of the present disclosure, those skilled in the art can readily clone the nucleic acid molecule and express the protein from the optimized gene sequence in the host cell using known molecular biology techniques, all without undue experimentation.

Embodiments of the present invention also relate to a nucleic acid molecule comprising the optimized gene sequence obtained from a method of the present invention, as well as vectors and host cells comprising the nucleic acid molecule of the present invention.

Various embodiments of the invention have now been described. It is to be noted, however, that this description of these specific embodiments is merely illustrative of the principles underlying the inventive concept. It is therefore contemplated that various modifications of the disclosed embodiments will, without departing from the spirit and scope of the invention, be apparent to persons skilled in the art.

The following specific examples of the methods of the invention are further illustrative of the nature of the invention, it needs to be understood that the invention is not limited thereto.

EXAMPLE

This example illustrates the optimization and expression of a gene sequence, e.g., human OCT 4 gene encoding POU class 5 homeobox 1, for recombinant expression in *E. coli*. Similar method can be used for optimization and expression of other genes in *E. coli* or other host cells.

The DNA sequence of the wild-type human OCT 4 gene (gi|261859841) (SEQ ID NO: 1) was subject to Particle Swarm Optimization (POS) analysis using a POS algorithm having an objective function F(x) as that described above. During the sequence optimization, the value of F(x) went up until it reached maximum, i.e., the global best, when the optimized OCT 4 gene sequence (SEQ ID NO:2) was obtained. A DNA molecule having the optimized OCT 4 gene sequence was synthesized using a known method.

Each of the wild-type human OCT 4 gene and the optimized OCT 4 gene was cloned into an inducible expression vector pET43a(+) (Invitrogen), using standard molecular biology techniques. Each of the expression vectors for the wild-type OCT 4 gene and the optimized OCT 4 gene was transformed into an *E. coli* host cell BL21(DE3), using standard molecular biology techniques. The resulting recombinant *E. coli* cells containing the expression vector were cultured under conditions inducible or non-inducible for the expression of the cloned OCT 4 gene. The total proteins in the cells were analyzed by SDS PAGE followed by Coomassie Blue Staining.

As shown in FIG. 1, when grown under conditions for induced expression of the cloned OCT 4 gene, the optimized OCT 4 gene resulted in significantly increased protein expression in the *E. coli* host cells.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A method for optimizing a gene sequence for expression of a protein in a host cell, the method comprising:
   (a) identifying a plurality of sequence factors that affect the expression of the protein in the host cell;
   (b) defining a computer-assisted particle swarm optimization algorithm comprising a function for each of the plurality of sequence factors; and
   (c) analyzing the gene sequence to obtain an optimized gene sequence for expression of the protein in the host cell via the computer-assisted particle swarm optimization algorithm that takes into account the plurality of sequence factors and achieves the maximum value of the swarm optimization algorithm to thereby obtain the optimized gene sequence,
   wherein the plurality of sequence factors comprises at least one factor that is not codon usage of the host cell.

2. The method of claim 1, wherein the plurality of sequence factors comprises at least two sequence factors selected from the group consisting of: codon usage of the host cell; tRNA usage of the host cell; GC-content of the gene sequence; a DNA cis-acting element of the gene sequence; a repetitive element of the gene sequence; a promoter of the gene sequence; 5'-UTR sequence; ribosome binding site (RBS) sequence; RNA splicing site sequence; 3'-UTR sequence; and an mRNA cis-element sequence.

3. The method of claim 2, wherein the DNA cis-element is selected from the group consisting of a TATA box, Pribnow box, SOS box, CAAT box, CCAAT box and an operator; the mRNA cis-element sequence is selected from the group consisting of a sequence of a ribosomal protein leader, a zip code motif, an mRNA stability element, an mRNA destability element, a translational repressor, a translational enhancer, a polyadenylation element that affects 3' UTR maturation, a splicing enhancer or silencer, and an internal ribosome entry site (IRES); and the ribosome binding site (RBS) is selected from the group consisting of Shine-Dalgarnon sequence (SEQ ID NO:1-AGGAGG), Kozak sequence, and a derivative thereof.

4. The method of claim 1, wherein the host cell is selected from the group consisting of a bacterial cell, a yeast cell, an insect cell and a mammalian cell.

5. The method of claim 1, wherein the particle swam optimization algorithm is defined as:

$$F(x) = f_{total}(x) - \sum_{i=1}^{p} \omega_i \times f_i(x) \quad (1)$$

wherein, $$f_{total}(x) = S_{codon} \times n \quad (2)$$

$f_{total}(x)$ is an initiation total score of the gene sequence; n is the length of the protein; and
$S_{codon}$ represents a function of codons within the protein;
p is the number of the identified plurality of sequence factors and p>1;
$f_i(x)$ denotes a function of the $i^{th}$ sequence factor of the identified p sequence factors;
$\omega_i$, denotes the relative weight given to $f_i(x)$; and
wherein the optimized gene sequence achieves the maximum value of F(x), and the method further comprising synthesizing a nucleic acid molecule comprising the optimized gene sequence.

6. The method of claim 5, wherein $f_i(x)$ comprises two or more selected from the group consisting of:
a function of direct repeats defined as $$f_1(x) = \sum_{i=1}^{c1} \sum_{j=1}^{l1} d_{ij} \quad (3)$$

wherein c1 is the number of occurrences of a direct repeat within the gene sequence, l1 is the length of the direct repeat, and $d_{ij}$ represents a score of the jth nucleotide in the ith direct repeat in the gene sequence;
a function of reverse repeats defined as $$f_2(x) = \sum_{i=1}^{c2} \sum_{j=1}^{l2} r_{ij} \quad (4)$$

wherein c2 is the number of occurrences of a reverse repeat within the gene sequence, l2 is the length of the reverse repeat, and $r_{ij}$ represents a score of the jth nucleotide in the ith reverse repeat in the gene sequence;
a function of dyad repeats defined as $$f_3(x) = \sum_{i=1}^{c3} \sum_{j=1}^{l3} dy_{ij} \quad (5)$$

wherein c3 is the number of occurrences of a dyad repeat within the gene sequence, l3 is the length of the dyad repeat, and $dy_{ij}$ represents a score of the jth nucleotide in the ith dyad repeat in the gene sequence;
a function of negative motifs defined as $$f_4(x) = \sum_{i=1}^{c4} \varepsilon_i \times s_{motif}^i \quad (6)$$

wherein c4 is the number of occurrences of a negative motif within the gene sequence, $\varepsilon_i$ is the corresponding weight given to the ith negative motif in the gene sequence, and $S_{motif}^i$ represents a score of the ith negative motif;
a function of used codon bias defined as $$f_5(x) = \left( \prod_{i=1}^{n} (f_{ik} / f_{imax}) \right)^{\frac{1}{n}} \quad (7)$$

wherein $f_{ik}$ represents the frequency of the kth synonymous codon of the ith amino acid of the protein, $f_{imax}$ represents the frequency of the most frequent synonymous codon of the ith amino acid of the protein, n is the length of protein sequence;
a function of undesirable splicing sites defined as $$f_6(x) = \sum_{i=1}^{c6} (x_i)^{\alpha - s6} \quad (8)$$

wherein c6 is the number of occurrences of an undesirable splicing site within the gene sequence, $x_i$ is the base of score function; $\alpha$ is a threshold of scoring the undesirable splicing site; s6 represents a score of the undesirable splicing site evaluated by a splicing site prediction system; and
a function of GC content defined as $$f_7(x) = \sum_{i=1}^{l-w} \left| v_{gc} - \sum_{j=1}^{w} \frac{c_j}{w} \right|_i \quad (9)$$

wherein l is the length of the gene sequence, $v_{gc}$ the cutoff value of ideal GC content for the host cell, $c_j$ is the number of occurrences of base G and C within the gene sequence, $c_j$ is 1 if the jth nucleotide is G or C, $c_j$ is 0 if the jth nucleotide is A or T.

7. The method of claim 5, wherein p is selected from the group consisting of 2, 3, 4, 5, 6, and 7.

8. A system for optimizing a gene sequence for expression of a protein in a host cell, the system comprising a computer system for applying a computer-assisted particle swarm optimization algorithm to the gene sequence to obtain an optimized gene sequence for expression of the protein in the host cell, wherein the computer-assisted particle swarm optimization algorithm comprises a function of each of a plurality of sequence factors that affect the expression of the protein in the host cell, and takes into account the plurality of sequence factors and achieves the maximum value of the swarm optimization algorithm to thereby obtain the optimized gene sequence, wherein the plurality of sequence factors comprises at least one factor that is not codon usage of the host cell.

9. The system of claim 8, wherein the plurality of sequence factors comprises at least two sequence factors selected from the group consisting of: codon usage of the host cell; tRNA usage of the host cell; GC-content of the gene sequence; a DNA cis-acting element of the gene sequence; a repetitive element of the gene sequence; a promoter of the gene sequence; 5'-UTR sequence; ribosome binding site (RBS) sequence; RNA splicing site sequence; 3'-UTR sequence; and an mRNA cis-element sequence.

10. The system of claim 8, wherein the particle swarm optimization algorithm is defined as:

$$F(x) = f_{total}(x) - \sum_{i=1}^{p} \omega_i \times f_i(x) \quad (1)$$

wherein, $$f_{total}(x) = S_{codon} \times n \quad (2)$$

$f_{total}(x)$ is an initiation total score of the gene sequence;
n is the length of the protein; and
$S_{codon}$ represents a function of codons within the protein;
p is the number of the identified plurality of sequence factors and p>1;
$f_i(x)$ denotes a function of the $i^{th}$ sequence factor of the identified p sequence factors; and
$\omega_i$ denotes the relative weight given to $f_i(x)$;
wherein the optimized gene sequence is obtained when F(x) reaches the maximum.

11. The system of claim 10, wherein $f_i(x)$ comprises two or more selected from the group consisting of:
a function of direct repeats defined as $$f_1(x) = \sum_{i=1}^{c1} \sum_{j=1}^{l1} d_{ij} \quad (3)$$

wherein c1 is the number of occurrences of a direct repeat within the gene sequence, l1 is the length of the direct repeat, and $d_{ij}$ represents a score of the jth nucleotide in the ith direct repeat in the gene sequence;
a function of reverse repeats defined as $$f_2(x) = \sum_{i=1}^{c2} \sum_{j=1}^{l2} r_{ij} \quad (4)$$

wherein c2 is the number of occurrences of a reverse repeat within the gene sequence, l2 is the length of the reverse repeat, and $r_{ij}$ represents a score of the jth nucleotide in the ith reverse repeat in the gene sequence;
a function of dyad repeats defined as $$f_3(x) = \sum_{i=1}^{c3} \sum_{j=1}^{l3} dy_{ij} \quad (5)$$

wherein c3 is the number of occurrences of a dyad repeat within the gene sequence, l3 is the length of the dyad repeat, and $dy_{ij}$ represents a score of the jth nucleotide in the ith dyad repeat in the gene sequence;
a function of negative motifs defined as $$f_4(x) = \sum_{i=1}^{c4} \varepsilon_i \times s_{motif}^i \quad (6)$$

wherein c4 is the number of occurrences of a negative motif within the gene sequence, $\varepsilon_i$ is the corresponding weight given to the ith negative motif in the gene sequence, and $S^i_{motif}$ represents a score of the ith negative motif;
a function of used codon bias defined as $$f_5(x) = \left(\prod_{i=1}^{n} (f_{ik} / f_{imax})\right)^{\frac{1}{n}} \quad (7)$$

wherein $f_{ik}$ represents the frequency of the kth synonymous codon of the ith amino acid of the protein, $f_{imax}$ represents the frequency of the most frequent synonymous codon of the ith amino acid of the protein, n is the length of protein sequence;
a function of undesirable splicing sites defined as $$f_6(x) = \sum_{i=1}^{c6} (x_i)^{a-s6} \quad (8)$$

wherein c6 is the number of occurrences of an undesirable splicing site within the gene sequence, $x_i$ is the base of score function; $\alpha$ is a threshold of scoring the undesirable splicing site; s6 represents a score of the undesirable splicing site evaluated by a splicing site prediction system; and
a function of GC content defined as $$f_7(x) = \sum_{i=1}^{l-w} \left| v_{gc} - \sum_{j=1}^{w} \frac{c_j}{w} \right|_i \quad (9)$$

wherein l is the length of the gene sequence, $v_{gc}$ is the cutoff value of ideal GC content for the host cell, $c_j$ is the number of occurrences of base G and C within the gene sequence, $c_j$, is 1 if the jth nucleotide is G or C, $c_j$, is 0 if the jth nucleotide is A or T.

12. The system of claim 10, wherein p is selected from the group consisting of 2, 3, 4, 5, 6, and 7.

13. A program product stored on a non-transitory computer readable medium for optimizing a gene sequence for expression of a protein in a host cell, the program product comprising: a computer software for applying a computer-assisted particle swarm optimization algorithm to the gene sequence to obtain an optimized gene sequence for expression of the protein in the host cell, wherein the particle swarm optimization algorithm comprises a function of each of a plurality of sequence factors that affect the expression of the protein in the host cell, the computer-assisted swarm optimization algorithm takes into account the plurality of sequence factors and achieves the maximum value of the swarm optimization algorithm to thereby obtain the optimized gene sequence, wherein the plurality of sequence factors comprises at least one factor that is not codon usage of the host cell.

14. The program product of claim 13, wherein the particle swarm optimization algorithm is defined as:

$$F(x) = f_{total}(x) - \sum_{i=1}^{p} \omega_i \times f_i(x) \quad (1)$$

wherein, $$f_{total}(x) = S_{codon} \times n \quad (2)$$

$f_{total}(x)$ is an initiation total score of the gene sequence;
n is the length of the protein; and
$S_{codon}$ represents a function of codons within the protein;
p is the number of the identified plurality of sequence factors and p>1;
$f_i(x)$ denotes a function of the $i^{th}$ sequence factor of the identified p sequence factors; and
$\omega_i$ denotes the relative weight given to $f_i(x)$;
wherein the optimized gene sequence is obtained when F(x) reaches the maximum.

15. The program product of claim 14, wherein $f_i(x)$ comprises two or more selected from the group consisting of:
a function of direct repeats defined as $$f_1(x) = \sum_{i=1}^{c1} \sum_{j=1}^{l1} d_{ij} \quad (3)$$

wherein c1 is the number of occurrences of a direct repeat within the gene sequence, l1 is the length of the direct repeat, and $d_{ij}$ represents a score of the jth nucleotide in the ith direct repeat in the gene sequence;
a function of reverse repeats defined as $$f_2(x) = \sum_{i=1}^{c2} \sum_{j=1}^{l2} r_{ij} \quad (4)$$

wherein c2 is the number of occurrences of a reverse repeat within the gene sequence, l2 is the length of the reverse repeat, and $r_{ij}$ represents a score of the jth nucleotide in the ith reverse repeat in the gene sequence;
a function of dyad repeats defined as $$f_3(x) = \sum_{i=1}^{c3} \sum_{j=1}^{l3} dy_{ij} \quad (5)$$

wherein c3 is the number of occurrences of a dyad repeat within the gene sequence, l3 is the length of the dyad repeat, and $dy_{ij}$ represents a score of the jth nucleotide in the ith dyad repeat in the gene sequence;
a function of negative motifs defined as $$f_4(x) = \sum_{i=1}^{c4} \varepsilon_i \times s_{motif}^i \quad (6)$$

wherein c4 is the number of occurrences of a negative motif within the gene sequence, $\varepsilon_i$ is the corresponding weight given to the ith negative motif in the gene sequence, and $S^i_{motif}$ represents a score of the ith negative motif;
a function of used codon bias defined as $$f_5(x) = \left( \prod_{i=1}^{n} (f_{ik} / f_{imax}) \right)^{\frac{1}{n}} \quad (7)$$

wherein $f_{ik}$ represents the frequency of the kth synonymous codon of the ith amino acid of the protein, $f_{imax}$ represents the frequency of the most frequent synonymous codon of the ith amino acid of the protein, n is the length of protein sequence;
a function of undesirable splicing sites defined as $$f_6(x) = \sum_{i=1}^{c6} (x_i)^{a-s6} \quad (8)$$

wherein c6 is the number of occurrences of an undesirable splicing site within the gene sequence, $x_i$ is the base of score function; $\alpha$ is a threshold of scoring the undesirable splicing site; s6 represents a score of the undesirable splicing site evaluated by a splicing site prediction system; and
a function of GC content defined as $$f_7(x) = \sum_{i=1}^{l-w} \left| v_{gc} - \sum_{j=1}^{w} \frac{c_j}{w} \right|_i \quad (9)$$

wherein l is the length of the gene sequence, $v_{gc}$ the cutoff value of ideal GC content for the host cell, $c_j$ is the number of occurrences of base G and C within the gene sequence, $c_j$ is 1 if the jth nucleotide is G or C, $c_j$ is 0 if the jth nucleotide is A or T.

16. The program product of claim 14, wherein p is selected from the group consisting of 2, 3, 4, 5, 6, and 7.

17. A method for expressing a protein in a host cell, the method comprising:
(a) obtaining an optimized gene sequence for expression of the protein in the host cell using a method of claim 1;
(b) synthesizing a nucleic acid molecule comprising the optimized gene sequence;

(c) introducing the nucleic acid molecule into the host cell to obtain a recombinant host cell; and
(d) cultivating the recombinant host cell under conditions to allow expression of the protein from the optimized gene sequence.

18. An isolated nucleic acid molecule comprising the optimized gene sequence obtained from the method of claim 1.

19. A vector comprising the isolated nucleic acid molecule of claim 18.

20. A recombinant host cell comprising the isolated nucleic acid molecule of claim 18.

* * * * *

SEQUENCE LISTING

```
<160> NUMBER OF SEQ ID NOS: 2

<210> SEQ ID NO 1
<211> LENGTH: 1080
<212> TYPE: DNA
<213> ORGANISM: Homo sapiens

<400> SEQUENCE: 1
atggcgggac acctggcttc ggatttcgcc ttctcgcccc ctccaggtgg tggaggtgat      60
gggccagggg ggccggagcc gggctgggtt gatcctcgga cctggctaag cttccaaggc     120
cctcctggag ggccaggaat cgggccgggg gttgggccag gctctgaggt gtgggggatt     180
cccccatgcc ccccgccgta tgagttctgt gggggatgg cgtactgtgg gccccaggtt      240
ggagtggggc tagtgcccca aggcggcttg gagacctctc agcctgaggg cgaagcagga     300
gtcggggtgg agagcaactc cgatgggcc tccccggagc cctgcaccgt caccctggt      360 gccgtgaagc tggagaagga gaagctggag caaaacccgg aggagtccca ggacatcaaa     420
gctctgcaga aagaactcga gcaatttgcc aagctcctga gcagaagag gatcaccctg     480
```

```
ggatatacac aggccgatgt ggggctcacc ctgggggttc tatttgggaa ggtattcagc    540
caaacgacca tctgccgctt tgaggctctg cagcttagct tcaagaacat gtgtaagctg    600
cggcccttgc tgcagaagtg ggtggaggaa gctgacaaca atgaaaatct tcaggagata    660
tgcaaagcag aaaccctcgt gcaggcccga agagaaagc gaaccagtat cgagaaccga     720
gtgagaggca acctggagaa tttgttcctg cagtgcccga aacccacact gcagcagatc    780
agccacatcg cccagcagct tgggctcgag aaggatgtgg tccgagtgtg gttctgtaac    840
cggcgccaga agggcaagcg atcaagcagc gactatgcac aacgagagga ttttgaggct    900
gctgggtctc ctttctcagg gggaccagtg tcctttcctc tggccccagg gccccatttt    960
ggtaccccag gctatgggag ccctcacttc actgcactgt actcctcggt cccttttcct   1020
gagggggaag cctttccccc tgtctccgtc accactctgg gctctcccat gcattcaaac   1080
```

<210> SEQ ID NO 2
<211> LENGTH: 1080
<212> TYPE: DNA
<213> ORGANISM: Artificial Sequence
<220> FEATURE:
<223> OTHER INFORMATION: Synthetic gene for human OCT 4 gene

<400> SEQUENCE: 2

```
atggccggtc atctggctag tgattttgca ttttctccgc cgccgggtgg tggtggcgat     60
ggcccaggtg gtccagaacc aggttgggta gatccacgca catggctgtc cttccagggt    120
ccgccaggtg gtccaggtat cggtccaggt gtaggtccgg gtagtgaagt atgggggtatc   180 ccgccatgtc caccgccgta cgaattctgt ggtggcatgg cttactgtgg tccgcaagta    240
ggtgtaggcc tggtaccaca gggtggtctg gaaacaagtc agccagaagg cgaggctggg    300
gtaggggtcg aatcgaattc agatggcgct agcccggagc catgcactgt aactccaggc    360
gccgtaaaac tggaaaaaga aaaactggag cagaatccag aagagtcgca agatatcaaa    420
gcactgcaaa aagagctgga acaatttgct aaactgctga acaaaaacg cattacgctg     480 ggttatacac aagccgacgt aggtctgaca ctgggggtcc tgttcggtaa agtattctcg    540
cagacaacaa tttgccgctt tgaagccctg cagctgtcat ttaaaaatat gtgtaaactg    600
cgcccactgc tgcagaaatg ggtagaggaa gccgacaaca acgagaatct gcaagagatt    660
tgtaaagctg aaacgctggt acaggcccgt aaacgtaaac gcacaagtat cgaaaatcgt    720
gtccgtggta acctggagaa tctgttcctg caatgtccaa aaccaacgct gcaacaaatc    780
tctcacatcg cacaacaact gggtctggag aaagactag tacgcgtatg gttctgtaac    840
cgccgccaga aagtaaacg tagtagtagc gattacgctc agcgcgaaga ctttgaagcc    900
gcaggtagtc cgttctccgg gggtccagta agtttcccac tggcaccggg tccacatttc    960
ggtacaccag gctacggttc tccgcacttt acagccctgt atagttcggt tccattcccg   1020
gaaggtgaag cttttccacc agtatccgta acaacgctgg ggtccccaat gcatagtaat   1080
```